United States Patent

Mulier et al.

Patent Number: 5,609,151
Date of Patent: Mar. 11, 1997

[54] METHOD FOR R-F ABLATION

[75] Inventors: Peter M. J. Mulier, St. Paul; Michael F. Hoey, Shoreview, both of Minn.

[73] Assignee: Medtronic, Inc., Minneapolis, Minn.

[21] Appl. No.: 303,246

[22] Filed: Sep. 8, 1994

[51] Int. Cl.$^6$ ............ A61B 5/04; A61B 17/39; A61N 1/05

[52] U.S. Cl. ............ 128/642; 606/27; 606/41; 607/99; 607/105; 607/113; 607/122; 607/127

[58] Field of Search ............ 606/41, 27; 128/642; 607/122, 127, 105, 113, 99

[56] References Cited

U.S. PATENT DOCUMENTS

| | | |
|---|---|---|
| 4,506,680 | 3/1985 | Stokes . |
| 4,920,980 | 5/1990 | Jackowski ............... 128/642 |
| 5,030,204 | 7/1991 | Badger . |
| 5,060,660 | 10/1991 | Gambale . |
| 5,083,565 | 1/1992 | Parins . |
| 5,104,393 | 4/1992 | Isner . |
| 5,122,137 | 6/1992 | Lennox . |
| 5,165,421 | 11/1992 | Fleischhaker . |
| 5,222,938 | 6/1993 | Behl ............... 607/105 |
| 5,281,213 | 1/1994 | Milder . |
| 5,334,193 | 8/1994 | Nardella ............... 607/122 |
| 5,348,554 | 9/1994 | Imran et al. ............... 606/41 |

FOREIGN PATENT DOCUMENTS

| | | |
|---|---|---|
| 1690786 | 11/1991 | U.S.S.R. ............... 607/122 |
| 9220290 | 11/1992 | WIPO ............... 606/27 |
| 9304724 | 3/1993 | WIPO . |

*Primary Examiner*—Lee S. Cohen

[57] ABSTRACT

A method and apparatus for ablation of body tissue. A catheter provided with a hollow needle is employed both for mapping the location to be ablated by injection of an excitability reducing agent and for ablating tissue, employing RF energy in conjunction with an injected, conductive fluid.

7 Claims, 6 Drawing Sheets

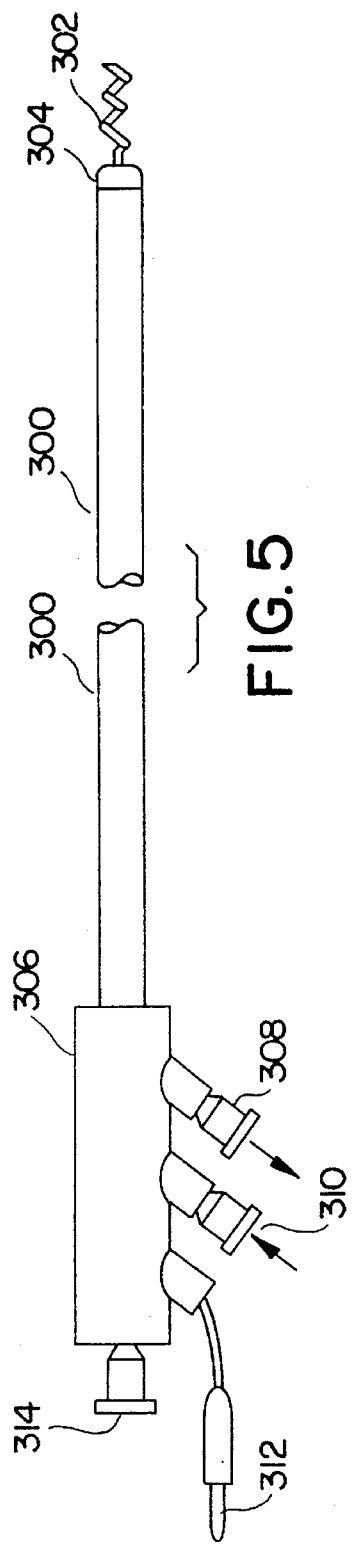
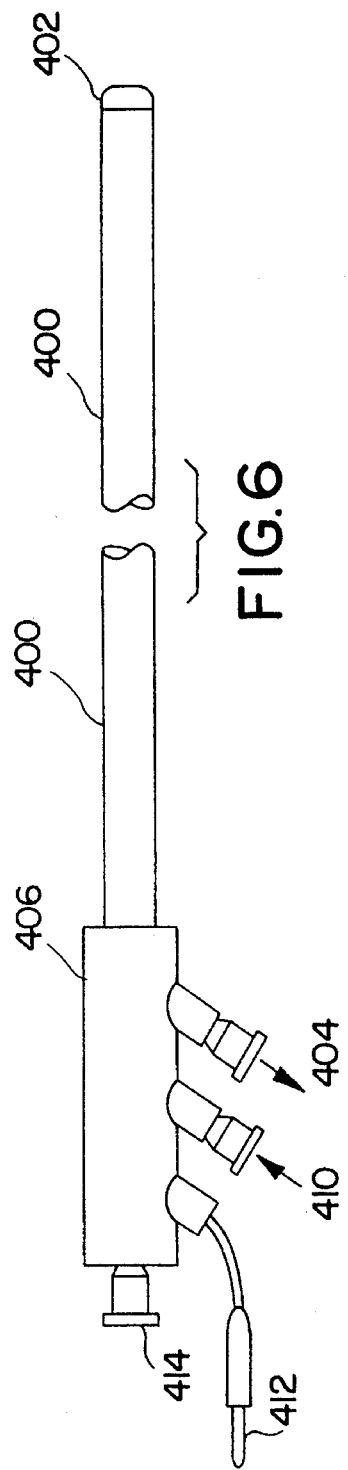
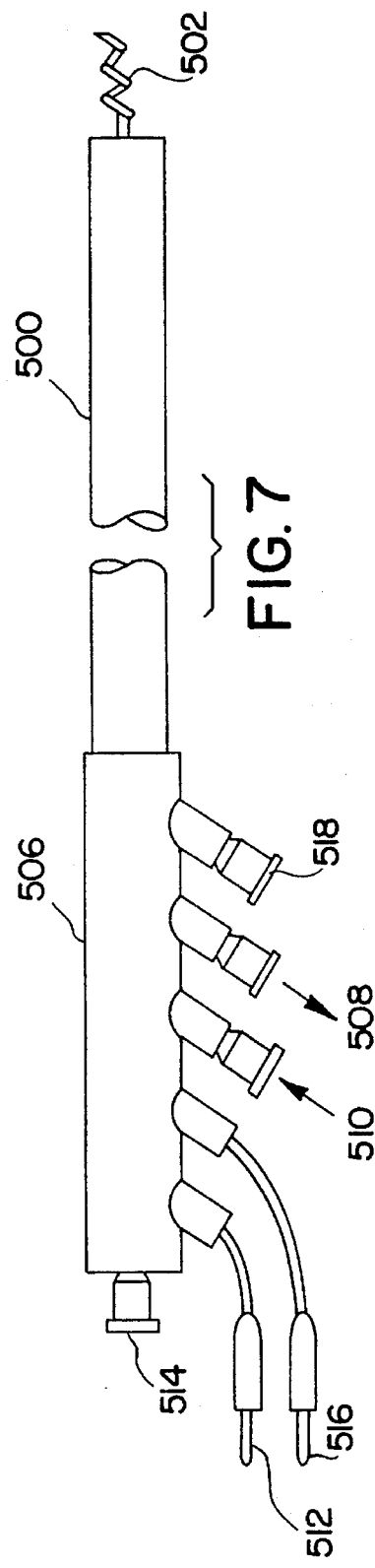

METHOD FOR R-F ABLATION

BACKGROUND OF THE INVENTION

This invention relates generally to the field of devices for cardiac surgery, and more specifically to devices for R-F ablation of cardiac tissue.

The present invention is directed toward treatment of tachyarrhythmias, which are heart rhythms in which a chamber or chamber of the heart exhibits an excessively fast rhythm. In particular, the present invention is directed toward treatment of tachycardias, which are due to the presence of ectopic foci within the cardiac tissue or due to the presence of aberrant conduction pathways within the cardiac tissue.

Therapies have been developed for treating tachycardias by destroying cardiac tissue containing identified ectopic foci or aberrant conduction pathways. A variety of approaches have been taken, including application of electrical energy or other forms of energy to destroy the undesired cardiac tissue. As examples, ablation of cardiac tissue has been accomplished by means of radio frequency electrical current, microwave energy, heat, electrical pulses, cryothermy, and lasers. At present, ablation using R-F energy is perhaps the most widely practiced in the context of ablation procedures that can be carried out by means of a catheter, inserted into the closed heart.

Most R-F ablation catheters employ electrodes which are intended to contact the endocardium of the heart, or, as in U.S. Pat. No. 5,083,565, are intended to penetrate the endocardium and enter the myocardium. In general, R-F ablation catheters are effective to induce small lesions in heart tissue including the endocardium and inner layers of myocardium, in the immediate vicinity of the electrode. However, the medical community has expressed a desire for devices which produce larger lesions, to reduce the number of applications of R-F energy (burns) required to effectively ablate the cardiac tissue associated with the tachycardia.

R-F ablation causes tissue in contact with the electrode to heat as a result of resistance of the tissue to the induced electrical current therethrough. The actual extent of heating is somewhat unpredictable. However, temperature tends to rise as the duration and amplitude of the R-F signal increase. Heating of the tissue beyond a certain point (i.e. 100 degrees C.) can cause dissection or charring of the tissue, resulting in a high impedance between the R-F electrode and the return electrode, which in turn leads to cessation of the heating process, and, in some cases, causes the electrode to stick to the charred tissue. One response to this phenomenon has been the inclusion of thermocouple within the ablation electrode, in conjunction with feedback control to modulate the R-F signal to maintain the electrode temperature at a set parameter. One such system is disclosed in U.S. Pat. No. 5,122,137.

SUMMARY OF THE INVENTION

The present invention is directed toward improving the consistency and efficacy of R-F ablation, by more accurately determining the ablation site and by increasing the overall size, extent and depth of the lesions induced by R-F ablation. These goals are pursued by means of an ablation catheter employing a hollow, preferably helical electrode intended to be placed against or preferably inserted into the myocardium or other tissue at the site intended for ablation. The electrode is provided with a source of physiologic Ringer's solution, saturated Ringer's solution or other conductive fluid for injection into the tissue adjacent the electrode. In its preferred embodiment, the conductive solution is applied through apertures at the end of or along the length of the electrode. The conductive solution injected prior to application of the R-F signal is believed to displace blood and/or increase the amount of intracellular in the vicinity of the electrode. Ringer's solution, for example, has a much higher conductivity than blood (approximately 3–4×) or cardiac muscle (approximately 7×), overall resistance to the induced electrical current is reduced, which is believed to assist in expanding the size of the lesion, by spreading the effective area of application of the electrical current over a wider area. Application of the conductive solution during the burn can also increase the thermal conductivity of the tissue 30–50%, and further assists in expanding the size of the lesion by preventing overheating of the tissue, allowing for a prolonged application of the R-F signal, extending beyond the point at which burning or charring would otherwise normally occur. Injection of a saturated Ringer's or saline solution has an even more dramatic effect, and produces a 10–15 fold increase over the level of conductivity provided by physiologic Ringer's solution. All of these factors are believed to contribute to an increase in the overall size of the lesion produced by application of R-F energy at a particular location.

In some embodiments, the catheter is also provided with a second electrode, recessed within a lumen open to the distal end of the catheter. The open end of the lumen is held against heart tissue by the helical electrode, and the lumen is filled with a conductive fluid which serves to couple the recessed electrode to the tissue. The two electrodes may be used alone or in conjunction with one another to produce lesions of varying shape and location.

In some embodiments, the catheter is adapted to deliver a chilled or heated fluid, such as Ringer's solution, through the electrode, onto or into the tissue adjacent the electrode. Chilled fluid may be used to cool the tissue in a fashion similar to cryo-mapping as disclosed in U.S. Pat. No. 5,281,213, issued to Milder et al. Typically, the temperature gradient provided by cryogenic cooling varies as a function of the thermal conductivity of the tissue, and the temperature gradient is typically quite steep. In the context of ablation of cardiac tissue, the ability to cool tissue deep in the ventricular wall has thus been limited by the requirement that the tissue adjacent the surface of the ventricular wall must not be cooled to the point of causing cellular damage. Injection of cooled fluid, such as Ringer's solution, serves to simultaneously cool the tissue and increase its thermal conductivity, with the net result that tissue deep in the ventricular wall can be cooled without cellular damage. In this context, directional injection of the chilled fluid through a laterally facing aperture in a hollow electrode, such as the opening at the distal end of a helical electrode, allows for testing of multiple adjacent tissue locations by simply rotating the electrode in the tissue, without having to reposition the catheter. Subsequent directional delivery of conductive fluid may also be employed in conjunction with ablation of the tissue.

Heated Ringer's or other conductive fluid may be delivered through the electrode to further enhance the R-F ablation process. By raising the temperature of the solution to 50 degrees centigrade or less, conductivity increases of up to 200% in the fluid itself and corresponding conductivity increases of up to 30% in the tissue in which the fluid is injected, can be achieved. Higher temperatures bring higher conductivities. Temperatures above 50 degrees centigrade, can cause ablation due to the heat of the delivered fluid as an adjunct to or a substitute for R-F ablation.

The catheters and electrodes disclosed are particularly optimized for ablation of heart tissue. However, the benefits provided by the present invention are believed equally valuable in applications related to ablation of other tissue types, and in particular are believed valuable in ablation of tumors. It is expected that electrode sizes and shapes, the conductivities, volumes and flow rates of the injected fluids, and the parameters of the R-F signal applied to the electrodes will vary as a function of the specific type of tissue being ablated.

BRIEF DESCRIPTION OF THE DRAWINGS

FIG. 5 illustrates an ablation catheter adapted to deliver a chilled fluid to its helical electrode, for mapping.

FIG. 6 illustrates an ablation catheter adapted to deliver a chilled fluid to a porous, non-helical electrode, for mapping.

FIG. 7 illustrates a second embodiment of an ablation catheter adapted to deliver a chilled fluid to its helical electrode, for mapping, which also employs a recessed, second electrode.

DETAILED DESCRIPTION OF THE PREFERRED EMBODIMENTS

Figure 1:
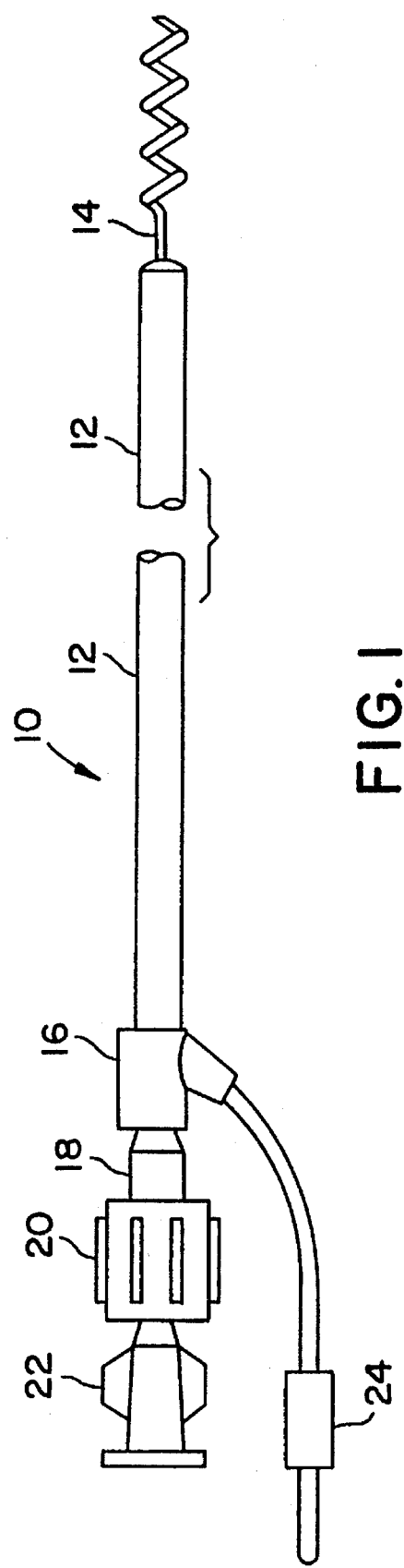
FIG. 1 is a plan view of a catheter adapted to perform the improved method of R-F ablation, according to the present invention.

FIG. 1 is a plan view of a catheter specifically designed for performing R-F ablation according to the present invention. The catheter includes an elongated catheter body 10, comprising an insulative outer sheath 12, which may be made of polyurethane, polytetraflouroethylene, or other biocompatible plastic. A hollow, helical electrode 14 is located at the distal end of the catheter and is coupled to the distal end of an internal tube, running the length of the catheter. At the proximal end of the catheter a fitting 16 is located, to which luer lock 18 is coupled. Luer lock 18 is coupled to the proximal end of the internal tube. A swivel mount 20 is mounted to luer lock 18, allowing rotation of the catheter relative to luer lock 22. Luer lock 22 is intended to be coupled to a source of conductive fluid such as Ringer's solution, and allows for application of the Ringer's solution through the catheter and through electrode 14, while electrode 14 is being screwed into heart tissue. An electrical connector 24 exits fitting 16, and is coupled to electrode 14, allowing for the use of electrode 14 to apply R-F energy to heart tissue. Electrode 14 may also be employed for other related functions such as measurement of electrograms within the heart and pacing of heart tissue by application of low energy pulses appropriate for cardiac pacing. In use, the catheter is advanced to the desired site for ablation, which preferably has been previously identified by means of cardiac mapping in a fashion similar to cardiac mapping presently employed with R-F ablation procedures. The catheter may be guided to the desired location by being passed down a steerable or guidable catheter, for example, as disclosed in U.S. Pat. No. 5,030,204, issued to Badger et al., or by means of a fixed configuration guide catheter, for example in U.S. Pat. No. 5,104,393, issued to Isner, both of which patents are incorporated herein by reference in their entireties. Alternatively, the catheter may be advanced to the desired site within a heart by means of a deflectable stylet, as disclosed in PCT Patent Application WO 93/04724, published Mar. 18, 1993, or a deflectable guidewire as disclosed in U.S. Pat. No. 5,060,660, issued to Gambale, et al., both of which patents are incorporated herein by reference in their entireties. When the hollow needle 14 is located at the desired location it is screwed into heart tissue by rotating the catheter body. A torque cable within the catheter body provides for 1:1 torque transfer from the proximal end of the catheter to the hollow needle 14.

When advanced to the desired location, luer lock 22 is coupled to a pressurized source of Ringer's or other conductive solution. An appropriate source is discussed in more detail in conjunction with FIG. 6 below. However, for purposes of the present invention, a source of Ringer's solution capable of delivering 2 cc per minute of solution at atmospheric pressure has been found to be adequate. Delivery of Ringer's solution should begin before or at the time at which the electrode 14 is screwed into the tissue to be ablated. In animal experimentation, the inventors have found that delivery of Ringer's solution for a period of five minutes prior to the delivery of R-F energy assists in producing a larger but still controlled, regular lesion.

After the electrode has been located, and Ringer's or other conductive solution has been administered for the desired period of time, electrical connector 24 is coupled to an R-F electrosurgical power source, of the type commercially available and employed for cutting, electro-coagulation or ablation. The present inventors have employed an Atakr Ablation System, manufactured by Cardiorhythm, San Hose, Calif., set to 50 watts output. At this setting, a prolonged application of R-F energy, e.g., for periods of two minutes, repeated immediately up to six times, may be employed to produce a large, controlled lesion. Greater or lesser time periods may be employed, however, time periods less than 20 seconds may be counter-indicated, as it appears that the cooling effect of the Ringer's solution, in such shorter R-F application times, may actually decrease the effective size of the lesion.

After R-F ablation, the electrode 14 may be coupled to a cardiac pacemaker, and cardiac pacing energy may be delivered to the lesion site in an attempt to measure the pacing threshold. Pacing threshold may be measured by delivering pacing pulses at differing energy levels, e.g. by altering pulse amplitude or width, and determining the minimum energy level effective to cause a depolarization of cardiac tissue. The inventors believe that the higher the pacing threshold, assuming a relatively homogenous lesion, the greater lesion size. As such, the electrode 14 can be used to derive a rough estimate of overall lesion size. The electrode 14 may also be coupled EKG monitoring equipment to assist in determining whether the tachycardia persists and whether the tissue in the vicinity of the electrode is still participating in aberrant conduction or ectopic activity, associated with the tachycardia.

The helical configuration of electrode 14 is believed to be particularly beneficial in the context of an ablation electrode. Because the electrode is screwed into and completely located within the heart tissue, out of the bloodstream, application of R-F energy is limited to the tissue itself. This differs from traditional R-F ablation electrodes, which simply contact the endocardium, with the result that a substantial portion of the energy applied is dissipated in the blood within the heart adjacent the electrode site. Moreover, R-F energy applied to the bloodstream may cause clotting of the blood adjacent the electrode, and raise the risk of clots breaking loose of the electrode.

The helical electrode also provides a substantially increased surface area as compared to the needle-like electrodes proposed in the above cited Parins patent, and also serves to anchor the catheter reliably during application of the R-F energy. In addition, the helical shape of the electrode prevents the application of conductive solution through the electrode from causing the electrode to be backed out of its insertion site due to hydraulic pressure, as might occur if a straight, hollow electrode were employed. The elongated path defined by the helical electrode also reduces the possibility of leakage of conductive fluid along the needle and out of the heart tissue.

Figure 2:
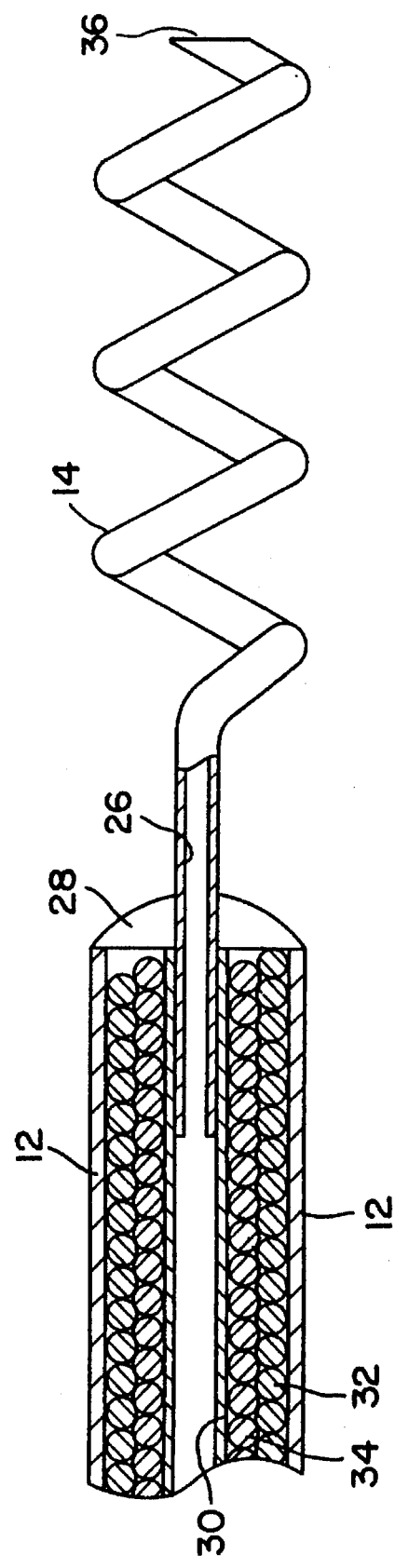
FIG. 2 is a cutaway view through the distal end of the catheter illustrated in FIG. 1.

FIG. 2 illustrates a cutaway version through the end of the catheter illustrated in FIG. 1. In this view, it can be seen that helical electrode 14 is provided with an internal lumen 26 which is in communication with the internal lumen of a tube 30. Tube 30 extends to the proximal end of the catheter and is in full communication with luer lock 18, as discussed above, tube 30 may be fabricated of polyamide tubing or of stainless steel tubing. In the present invention, the stainless steel tubing serves as an additional conductor, coupling electrode 14 to electrical connector 24 and enhancing the overall conductivity of the catheter. The use of polyamide tubing, while reducing the overall conductivity of the catheter enhances the flexibility somewhat, and may be beneficial in some cases. It is recommended to apply a steady flow of Ringer's solution through the tubing to electrode 14 during passage catheter through the vascular system to the electrode site, if possible. The flow of Ringer's solution in this case assists in maintaining the patency of the lumen of tubing 30, and prevents plugging of the exit ports of the electrode as it is advanced into the cardiac muscle.

Surrounding tube 30 are two coils 32 and 34, which are wound in opposite directions, to provide a torque cable. In the case of the specific devices employed by the inventors, a torque cable as manufactured by Lake Region Manufacturing Company of Chaska, Minn. was employed, which torque cable is described in U.S. Pat. No. 5,165,421, incorporated herein by reference in its entirety. Coils 32 and 34 also serve as conductors. As illustrated, tubing 30 is between metal coils 32 and 34 and helical electrode 14. However, if polyamide tubing is used, the coils 32 and 34 will serve as the only conductor and thus will be electrically coupled to electrode 14 by means of welding, soldering or mechanical interconnection. Insulative sleeve 12 serves both to provide a smooth exterior for the catheter and to insulate the metal coils 32 and 34, along the length of the catheter.

Electrode 14 comprises a hollow metal (e.g. stainless steel) tube, which may have only a single exit port 36, located as its distal end, or alternatively may be provided with a plurality of ports, arranged around and along the length of electrode 14. If directional injection of fluid is desired, typically only port 36 will be present. If an even distribution of fluid is desired, ports will be added to or substituted for port 36.

If desired, an insulative sleeve (not illustrated) which covers the proximal portion of the electrode may be provided, which serves to limit the application of R-F energy to the distal portion of the electrode. Exit ports may be limited to the exposed, uninsulated portion of electrode 14, or may extend along the entire length of electrode 14. If desired, a thermocouple or other temperature sensing device may be located within or attached to the electrode 14, to allow for temperature based feedback control of the R-F power applied to the electrode as described in the above-cited patent issued to Lennox et al.

Figure 3:
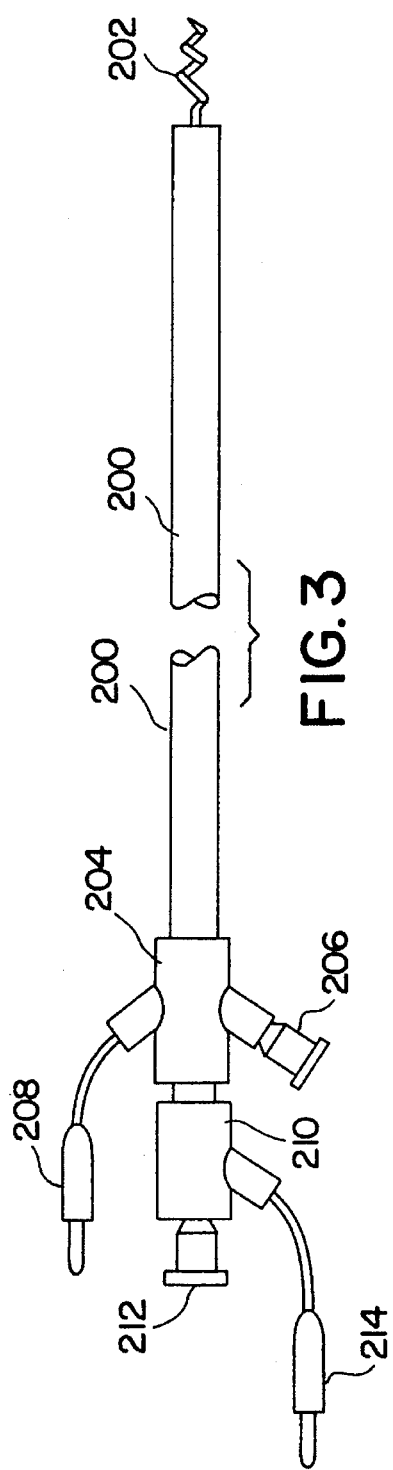
FIG. 3 illustrates an alternative embodiment to the catheter of FIGS. 1 and 2, employing a second, recessed electrode.

FIG. 3 illustrates a catheter employing a second, recessed electrode in addition to a penetrating, helical electrode 202 corresponding to electrode 14 as illustrated in FIG. 1. Electrode 202 protrudes out the distal end of the outer catheter sheath 200, which in turn is coupled to manifold 204, which includes a fluid fitting 206 and an electrical connector 208. Extending proximal to manifold 204 is a second manifold 210, preferably mounted rotatably with regard to manifold 204, and carrying a second fluid coupling 212 and a second electrical connector 214. Electrical connector 214 is coupled to electrode 202, and corresponds to electrical connector 24 of the device illustrated in FIG. 1. Fluid coupling 212 corresponds to luer lock 22 illustrated in FIG. 1, and is employed to deliver Ringer's or other fluid to the interior of electrode 202.

Figure 4:
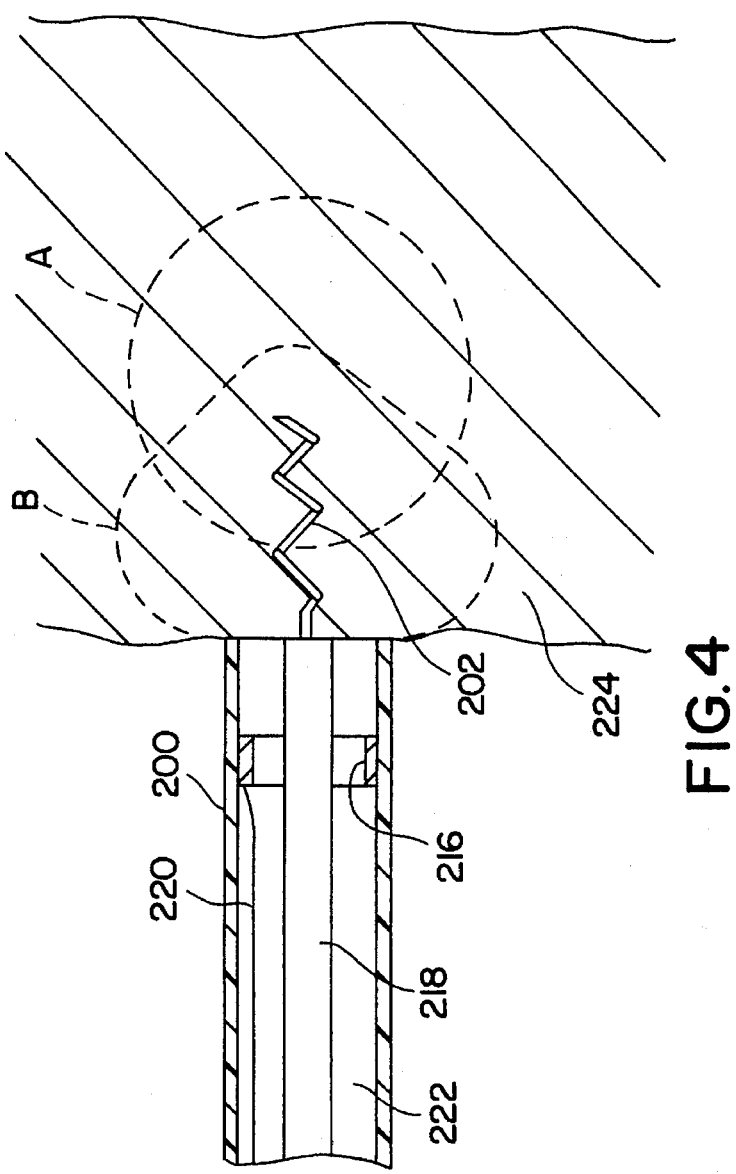
FIG. 4 illustrates a cut-away view of the catheter of FIG. 3, with its helical electrode located in heart tissue.

FIG. 4 shows a cutaway view of the distal end of the catheter illustrated in FIG. 3, with the electrode 202 screwed into heart tissue 224. In this view, it can be seen that within the outer catheter tube 200 is a second catheter body 218, which may correspond precisely to the body of the catheter illustrated in FIG. 1, and includes an internal lumen coupled to fluid connector 212 and to the interior of electrode 202, as well as an electrical conductor, for coupling electrode 202 to electrical connector 214.

Mounted within outer catheter tube 200 is an internal, recessed electrode 216 which is coupled to electrical connector 208 by means of an insulated conductor 220. In use, electrode 202 is screwed into heart tissue 224, holding the distal end of outer catheter tube 200 tightly adjacent the tissue. Lumen 222 may then be filled with Ringer's solution, providing a conductive connection between the ring electrode 216 and the heart tissue 224. Electrodes 216 and 202 may be used individually or in conjunction with one another, to control the depth and shape of the lesion provided.

A typical lesion outline for the helical electrode 202 is illustrated by broken line at A, while a typical lesion outline for the recessed electrode 216 is illustrated at broken out line at B. The lesions produced by recessed electrode 216 tend to be conically shaped, and located more closely adjacent the surface of the tissue. The lesions produced by electrode 202 tend to be more spherical or ovoid in configuration, and tend to be located deeper within the tissue.

FIG. 5 illustrates embodiment of a catheter particularly adapted for use in delivery of a chilled or a heated fluid through its helical electrode 302, to accomplish cardiac mapping, prior to ablation or to enhance conductivity during ablation, respectively. The catheter is provided with an elongated outer catheter tube 300, which terminates in a molded plastic member 304, from which the helical electrode 302 emerges. At its proximal end, a manifold 306 is coupled to outer catheter tube 300 and is provided with fluid couplings 308 and 310, for the ingress and egress, respectively, of a cooling or heating fluid. Manifold 306 is also provided with an electrical connector 312 which is coupled electrically to helical electrode 302 and with a fluid coupling 314 which is coupled to the interior of electrode 302, and is used to deliver Ringer solution through electrode 302.

Figure 8:
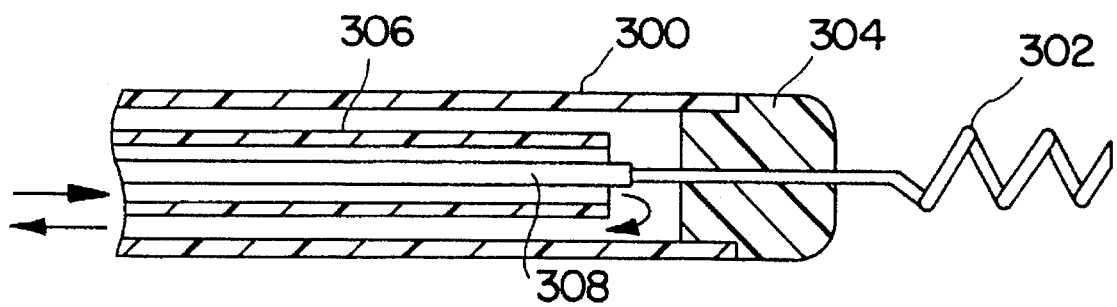
FIG. 8 illustrates a cut-away view through the distal portion of the catheter illustrated in FIG. 5.

A cutaway view through the distal portion of the catheter illustrated in FIG. 5 is shown in FIG. 8. In this view, it can be seen that located within outer catheter tube are an inner catheter tube 306 and a metal tube 308, fabricated, for example of stainless hypodermic tube, which serves to electrically couple electrode 302 to electrical connector 312 and to provide a fluid pathway from fluid coupling 314 to the interior of electrode 302. Plastic member 304 seals the distal end of the catheter body to the electrode 302.

Figure 12:
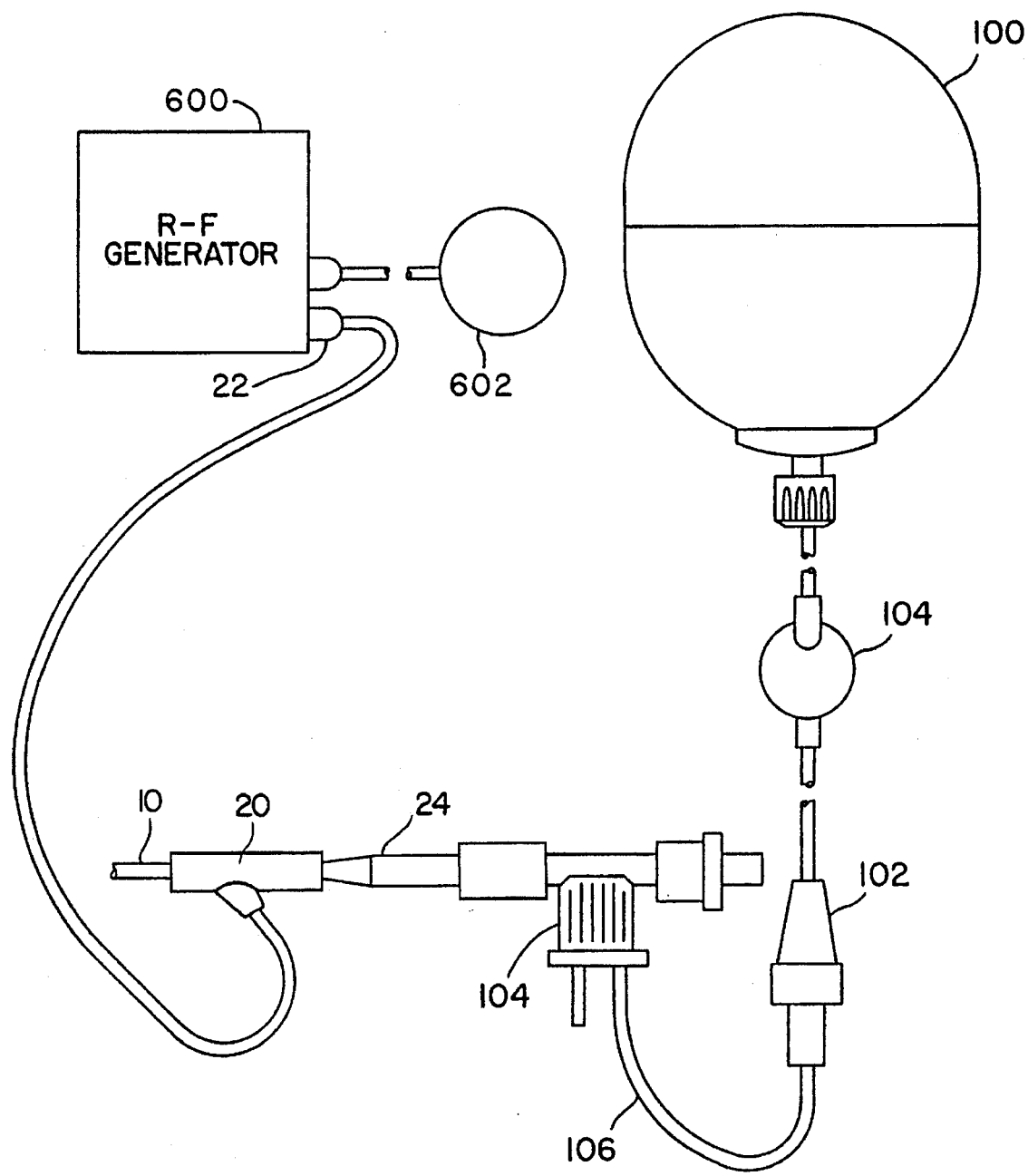
FIG. 12 illustrates a pressurized source for Ringer's solution which may be employed in conjunction with the catheters in FIGS. 1–11.

The inventors have determined that it is difficult to inject chilled or heated fluids down the length of the catheter as illustrated in FIG. 1 and FIG. 2, without the chilled or heated solution approaching body temperature by the time it reaches the helical electrode. As a result, as illustrated in FIG. 8, the inventors have derived a catheter which provides for three fluid flow channels, arranged concentrically. The inner channel, defined by the hypo tubing 308 serves to deliver the fluid to be heated or cooled(e.g. Ringer's solution) to the tissue, through electrode 302. The second fluid pathway, defined by the space between the inner tubing 306 and the hypo tubing 308, is coupled to fluid coupling 310, which in turn is to be coupled to a pumping means for pumping chilled or heated saline or other fluid down the catheter body, through this intermediate lumen, in order to keep the Ringer's solution within hypo tube 308 in a chilled or heated state. At the distal end of the catheter, the cooling fluid leaves the intermediate lumen and enters the outer lumen defined by the space between outer catheter tube 300 and inner catheter tube 306, where it travels back up the catheter proximally, to fluid coupling 308, for recirculation or disposal. A pressurized source for Ringer's solution to be injected into the tissue is illustrated in FIG. 12, and would be coupled to fluid fitting 314, illustrated in FIG. 5. Any appropriate pumping mechanism may be used to deliver heating or cooling fluid to fluid coupling 310 and to remove it from fluid coupling 308.

For purposes of mapping, it is preferred that the fluid delivered to the helical electrode 302 and injected into the tissue be no more than 5° C. In order to accomplish this, the temperature of the coolant fluid applied to fluid coupling 310 should be adjusted. If desired, a thermocouple, as discussed above, might optionally be employed in conjunction with electrode 302, and employed for temperature controlled regulation of the coolant temperature, as well as for temperature based feedback regulation of our power applied to the electrode ablation.

Tissue mapping using the catheter of FIG. 5 is accomplished by screwing the electrode 302 into the tissue to be tested, followed by delivery of chilled Ringer's solution at 5° C. or less, in order to slow conduction through the tissue, and monitoring the electrical activity of the heart by means of electrode 302, through electrical connector 312 (FIG. 5), while the patient is undergoing an episode of spontaneous or induced tachyarrhythmia. If cooling of the tissue terminates the arrhythmia, the site is identified as an appropriate location for RF ablation.

Figure 11:
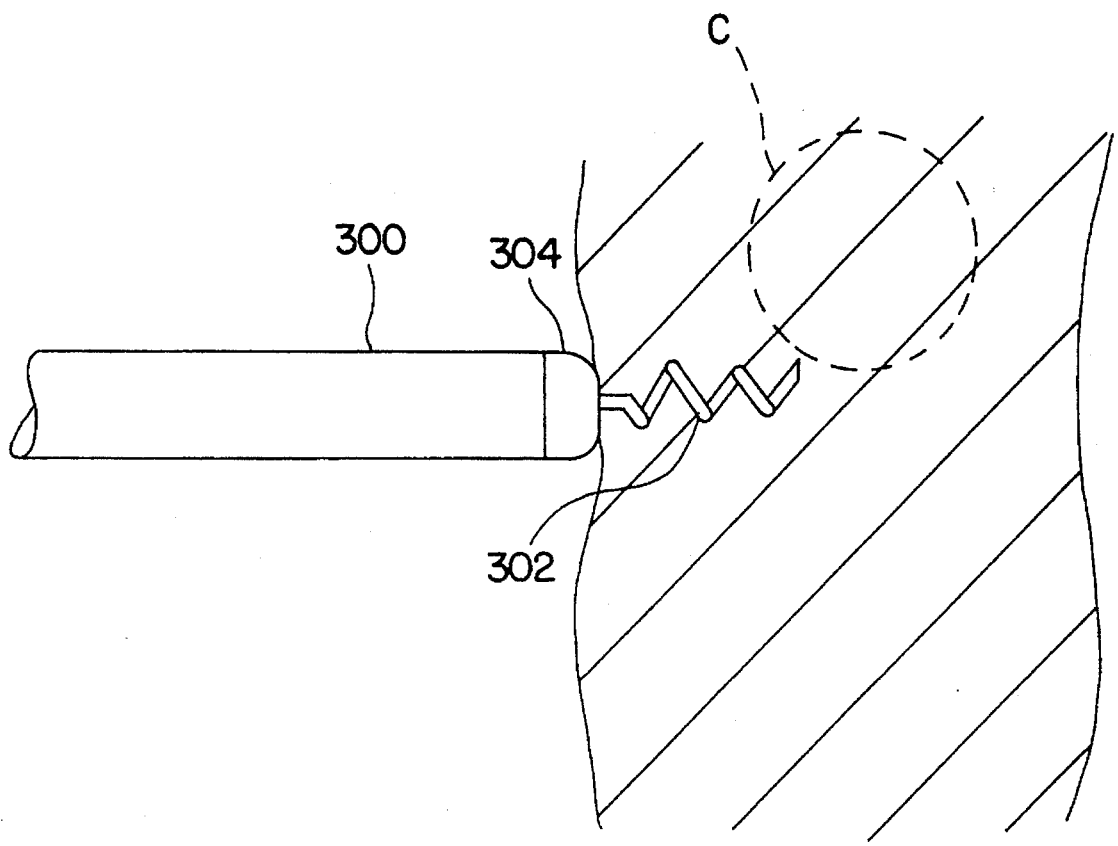
FIG. 11 illustrates a the distal portion of the catheter illustrated in FIG. 5, with its helical electrode located in heart tissue for directional mapping.

If the electrode 302 is provided with only a single aperture, or with apertures directed only in a single direction, the catheter may be used to map multiple adjacent tissue sites, as illustrated in FIG. 11. FIG. 11 shows the distal end of the catheter illustrated in FIG. 8, screwed into heart tissue. As illustrated at broken-out line C, chilled saline injected through the aperture at the distal end of the helix tends to enter the tissue in a single direction. By rotating the helix, while in the tissue, multiple adjacent tissue sites may be sequentially mapped, without the necessity of removing the catheter from the tissue. RF energy may subsequently be applied, along with directional injection of Ringers, in order to ablate the identified arrhythmogenic tissue.

Figure 9:
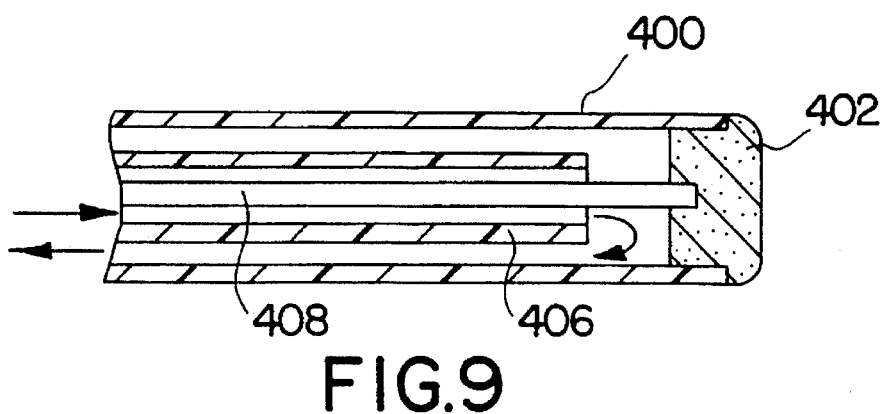
FIG. 9 illustrates a cut-away view through the distal portion of the catheter illustrated in FIG. 6.

FIG. 9 illustrates an alternative version of a mapping/ablation catheter differing from that illustrated in FIG. 8 primarily in that rather than a helical electrode 302 (FIG. 8), a porous electrode 402 is provided, mounted to the distal end of the outer catheter tube 400. Porous electrode 402 is preferably fabricated by powder metallurgy techniques, similar to those described in conjunction with U.S. Pat. No. 4,506,680, issued to Stokes and incorporated herein in its entirety, and is provided with a porosity which provides a high resistance to fluid flow, for example no more than X cc's of fluid per minute at a pressure of Y psi. Electrode 402 is coupled electrically to electrical connector 412 and is coupled to a length of hypo tubing within outer catheter body 400, which is in turn coupled to fluid coupling 414. Fluid couplings 410 and 408, on manifold 406 correspond to fluid couplings 308 and 310, mounted on manifold 306, in FIG. 5.

FIG. 9 shows a cutaway version through the distal portion of the catheter illustrated in FIG. 6, and in this view it can abe seen that its internal structure is similar to that of the catheter illustrated in FIG. 8. A length of hypo tubing 408 is coupled to electrode 402, providing both a fluid pathway to the electrode and an electrical connection to the electrode. Coolant enters the catheter through fitting 410, and flows down the catheter between inner catheter tube 306 and hypo tube 408. Coolant exits the catheter flooding proximally between outer catheter tube 400 and inner catheter tube 406.

In the context of the present invention, the provision of a porous electrode 402 having a high resistance to fluid flow prevents the delivered chilled fluid from simply leaking out and being washed away in the blood stream. By restricting the flow through the electrode, the electrode can be cooled to a degree which will allow its use for mapping purposes. The catheter may also be employed for ablation, with delivery of Ringer's solution or other fluid through hypo tube 408 being employed primarily to prevent overheating of electrode 402. As in conjunction with the embodiments of the present invention employing helical electrodes, electrode 402 might also optionally be provided with a thermocouple, allowing for temperature control feedback of electrode temperatures during both mapping and ablation.

FIG. 7 illustrates a second embodiment of a catheter, employing features of the catheters illustrated in FIGS. 3 and 5, in a single device. Outer catheter tube 500 carries a manifold 506 at its proximal end, which includes fluid couplings 508 and 510, for egress and ingress, respectively, of cooling or heating fluid. Electrical connector 512 is coupled to helical electrode 502. Fluid coupling 514 is coupled to the interior of electrode 502, allowing for delivery of Ringer's solution to the tissue, through electrode 502. Electrical connector 516 corresponds functionally to electrical connector 208 in FIG. 3, and is coupled to a recessed electrode located within outer catheter tube 500. Fluid coupling 518 corresponds functionally to fluid coupling 206 illustrated in FIG. 3, and serves to allow delivery of Ringer's solution within the outer catheter tube 500, in order to couple the recessed electrode tube, in the same fashion as discussed in conjunction with FIG. 4, above.

Figure 10:
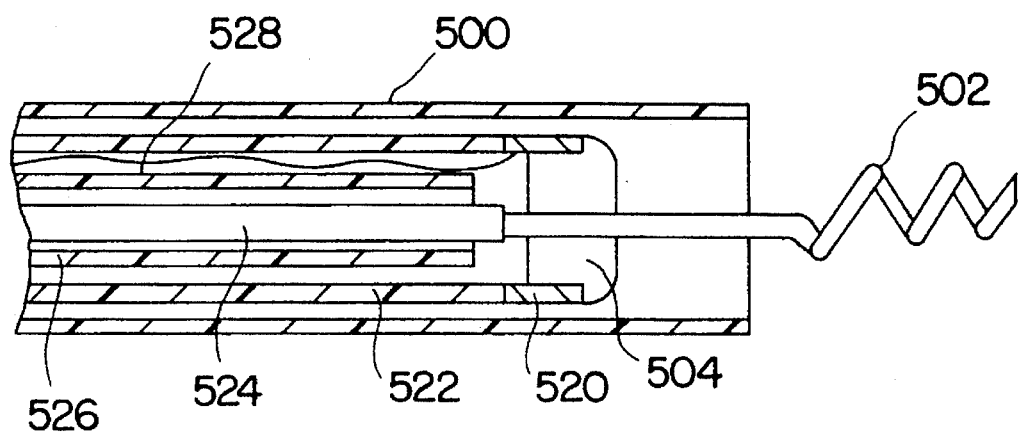
FIG. 10 illustrates a cut-away view through the distal portion of the catheter illustrated in FIG. 7.

FIG. 10 is a cutaway view through the distal end of the catheter illustrated in FIG. 7. In this version of the invention, the catheter defines four concentric fluid paths. The innermost fluid path is defined by hypo tubing 524 which is coupled to helical electrode 502. Ringer's solution is delivered from fluid coupling 514, through tube 524 to electrode 502. Tube 524 also is coupled to electrical connector 512. Mounted around tube 524 is inner catheter tube 526, which corresponds functionally to inner catheter tubes 306 and 406 as illustrated in FIGS. 8 and 9, respectively. Cooling or heating fluid flows distally through the catheter in the fluid space defined between inner catheter tube 526 and hypo tube 524. Intermediate catheter tube 522 surrounds inner catheter tube 526, and the space there between defines the return fluid flow path for coolant fluid, which is in turn coupled to fluid coupling 508. Plastic number 504 corresponds to plastic number 304 in FIG. 8, and serves to seal the distal end of intermediate catheter tube 522. A ring electrode 520 is mounted around plastic number 502 and is coupled to electrical connector 516 by means of insulative conductor 528. The space between outer catheter tube 500 and intermediate catheter tube 522 defines the fourth, concentric fluid flow path, and is coupled to fluid coupling 518, allowing for injection of Ringer's solution into the interior of outer catheter tube 500, which in turn serves to couple electrode 520 to cardiac tissue, in the same fashion as discussed in conjunction with the catheter illustrated in FIGS. 3 and 4.

After mapping, and after the tissue has warmed, ablation may be accomplished in the same fashion as discussed above in conjunction with the catheter illustrated in FIGS. 1 and 2. Alternatively, the catheters of FIGS. 5 and 7 may be employed to deliver heated Ringer's solution through the helical electrodes to further enhance conductivity. As noted above, heated Ringer's solution displays an increased conductivity as compared to body temperature fluid. In addition, with fluid temperatures of 50 degrees C. or above the heated fluid itself serves to ablate tissue, even in the absence of R-F energy. Any appropriate commercially available heating or cooling bath may be employed to regulate the temperature of the applied solution.

FIG. 12 illustrates a pressurized source for Ringer's or saline solution which may be employed to deliver solution to the electrodes of the catheters described above. A reservoir 100 is provided, which is commercially manufactured by Block Medical Inc., and sold under the brand name "Home Pump". The reservoir contains Ringer's solution or other conductive fluid and provides the fluid at one atmosphere pressure to flow control 102, via filter 104. Flow control 102 may, for example, provide a flow limit of 40 drops or 2 cc per minute. Flow control 102 is coupled to a second flow control element 104, which, in the experimental apparatus employed by the inventors allows for additional adjustability of flow rates. Flow control 102 or 104 preferably includes a one-way valve, providing a fluid column which prevents tissue from entering and plugging of the holes in the electrode. Flow control 104 is coupled to the luer lock 22, illustrated in FIG. 1, which in turn is in fluid communication with electrode 14 (FIG. 1), allowing delivery of Ringer's solution to the electrode. An electrosurgical generator 602 for providing R-F electrical energy is illustrated in functional block form, coupled to electrical connector 24 and to a ground plate electrode 602 (not drawn to scale). All other labeled elements correspond to those illustrated in FIG. 1.

While the embodiment illustrated above requires a second element (e.g. a guide catheter or guide wire) for advancing and positioning the catheter at its desired location, it is anticipated that the basic apparatus disclosed above may also be incorporated into catheters which themselves are steerable or deflectable, similar to R-F ablation catheters presently in clinical investigation. Similarly, it is anticipated that in commercial embodiments, alternative mechanisms (e.g. precision pumps) for controlling the flow of Ringer's solution may be employed. Similarly, while the inventors have employed Ringer's solution, other alternative fluids may be workable as well. As such, the embodiment discussed above should be considered exemplary, rather than limiting, in conjunction with the following claims.

In conjunction with the above specification, we claim:

1. A method of mapping cardiac tissue, comprising:

advancing an elongated catheter including a catheter body having proximal and distal ends comprising a first tube having an internal longitudinal lumen open to the distal end of said catheter body to a desired tissue location;

delivering fluid to said internal lumen and to said desired tissue location through said internal lumen;

cooling said fluid while in said internal lumen; and monitoring the response of said tissue to said cooled fluid.

2. A method according to claim 1, wherein;

said advancing step comprises advancing a catheter provided with a hollow needle coupled to the distal end of said internal lumen to said desired tissue location and penetrating tissue with said needle; and wherein said delivering step comprises delivering said fluid into said tissue through said needle.

3. A method according to claim 2, wherein;

said advancing step comprises advancing a catheter provided with a hollow helical needle coupled to the distal end of said internal lumen to said desired tissue location and screwing said helical needle into said tissue.

4. A method of ablating tissue, comprising:

advancing an elongated catheter including a catheter body having proximal and distal ends and having an internal longitudinal lumen and a hollow conductive electrode mounted to the distal end of said catheter body and having an internal lumen coupled to the internal lumen of said catheter body to a desired tissue location;

delivering a conductive fluid to said internal lumen of said catheter body and to said desired tissue location through said internal lumen of said electrode;

heating said fluid while in said internal lumen of said catheter body; and delivering R-F energy to said electrode.

5. A method according to claim 4, wherein;

said advancing step comprises advancing a catheter provided with a hollow needle coupled to the distal end of said internal lumen of said catheter body to said desired tissue location and penetrating tissue with said needle; and wherein said delivering step comprises delivering said fluid into said tissue through said needle.

6. A method according to claim 5, wherein;

said advancing step comprises advancing a catheter provided with a hollow helical needle coupled to the distal end of said internal lumen of said catheter body to said desired tissue location and screwing said helical needle into said tissue.

7. A method of ablating tissue comprising:

advancing an elongated catheter including a catheter body having proximal and distal ends and having an internal longitudinal lumen and a hollow member mounted to the distal end of said catheter body and having an internal lumen coupled to the internal lumen of said catheter body to a desired location and inserting said hollow member into tissue;

delivering a fluid to said internal lumen of said catheter body and to said desired location through said hollow member; and heating said fluid while in said internal lumen of said catheter body.

\* \* \* \* \*